United States Patent [19]

Balzer

[11] Patent Number: 5,098,596

[45] Date of Patent: Mar. 24, 1992

[54] DETERGENT COMPOSITIONS CONTAINING A CARBOXYMETHYLATED ETHOXYLATE WITH ELEVATED VISCOSITY

[75] Inventor: Dieter Balzer, Haltern, Fed. Rep. of Germany

[73] Assignee: Huels Aktiengesellschaft, Marl, Fed. Rep. of Germany

[21] Appl. No.: 444,427

[22] Filed: Dec. 1, 1989

[30] Foreign Application Priority Data

Feb. 25, 1989 [DE] Fed. Rep. of Germany ....... 3905938

[51] Int. Cl.$^5$ .................... C11D 1/74; C11D 10/02
[52] U.S. Cl. .................. 252/174.21; 252/173; 252/174.25; 252/174.22; 252/DIG. 14; 252/179.14; 252/547; 252/550
[58] Field of Search ............ 252/DIG. 14, 174.21, 252/173, 174.14, 174.25, 174.22

[56] References Cited

U.S. PATENT DOCUMENTS 4,485,873 12/1984 Balzer et al. ................ 166/274
4,781,207 11/1988 Balzer .................... 137/13

FOREIGN PATENT DOCUMENTS 1232817  2/1988  Canada .
 154380  9/1985  European Pat. Off. .
  23683  8/1975  Japan .
  49597 11/1983  Japan .
 158298  8/1985  Japan .

Primary Examiner—Prince Willis, Jr.
Assistant Examiner—James M. Silbermann
Attorney, Agent, or Firm—Oblon, Spivak, McClelland, Maier & Neustadt

[57] ABSTRACT

Aqueous detergent compositions containing
a) 5 to 30 wt. % of a carboxymethylated ethoxylate of Formula (I)

$$R-O-(C_2H_4O)_n CH_2 COOM \qquad (I),$$

in which R is a monounsaturated or polyunsaturated, branched or unbranched aliphatic group with 10 to 22 carbon atoms, n is an integer of 1 to 10, and M is an alkali metal, alkaline earth metal, ammonium, or alkylammonium ion;

b) 0 to 20 wt. % of a carboxymethylated ethoxylate of Formula II $$R'-O-(C_2H_4O)_m CH_2 COOM' \qquad (II),$$

in which R' is a saturated, branched or unbranched aliphatic group with 10 to 22 carbon atoms, or an alkylaromatic group with 8 to 18 carbon atoms in the alkyl group, m is an integer of 1 to 10, and M' is an alkali metal, alkaline earth metal, ammonium, or alkylammonium ion;

c) 0.2 to 6 wt. % of an electrolyte; and
d) water to make 100 wt. %, have elevated viscosities and are suitable for use in liquid cleansing agents and as the base for shampoos, bath and shower gels and other cosmetic formulations.

13 Claims, No Drawings

DETERGENT COMPOSITIONS CONTAINING A CARBOXYMETHYLATED ETHOXYLATE WITH ELEVATED VISCOSITY

BACKGROUND OF THE INVENTION

1. Field of the Invention

The present invention relates to aqueous detergent compositions with elevated viscosity for use in liquid cleansing agents and as the base for shampoos, bath and shower gels, and other cosmetic formulations in which elevated viscosity is required.

2. Discussion of the Background

Such systems in the past have been based primarily on alkyl sulfates or alkyl ether sulfates with usually low degrees of ethoxylation. The viscosity can then be adjusted relatively easily by adding sodium chloride, ammonium chloride, sodium sulfate and other electrolytes, possibly in combination with fatty acid diethanolamides and/or other additives. Such formulations show satisfactory foam, and they are economical, but they have the serious drawback of generally severe skin irritation and poor tolerability in the mucous membranes of the eye, which is of considerable importance considering that they are frequently used daily. Added to this is the problem, that has become important recently, of possible toxic effects from the dioxane content of ether sulfates and the N-nitrosamine content of fatty acid amides, so that formulations free of nitrogen without using ether sulfates are desirable. The remaining alkyl sulfates are among the surfactants with the lowest skin and mucous membrane tolerability.

The search for milder surfactants that do not have the above-mentioned drawback has been in progress for some time. Surfactants have actually been found that are acceptable to the skin and mucous membranes, but, on the other hand, they have the drawback that they cannot be thickened with electrolytes, or only to a very limited extent [see: H. Meijer, *Seifen-Öle-Fette-Wachse*, vol. 113, 135 (1987), and H. Tesmann, *Parfümerie und Kosmetik*, vol. 68, 630 (1987)]. It has therefore been attempted to produce sufficiently high viscosities by substituting a milder, toxicologically more acceptable, but unfortunately only very poorly thickenable surfactant for a very limited portion of the alkyl sulfate or of the ether sulfate (see U.S. Pat. No. 3,038,862 and H. Meijer, loc. cit.). Thickening by means of water-soluble polymers is of limited suitability because of the negative effect on foam quality and the feeling on the skin.

Thus, there remains a need for thickenable detergent compositions acceptable to the skin and mucous membranes of the eye that are largely free of alkyl or alkyl ether sulfates and of surfactants containing nitrogen.

SUMMARY OF THE INVENTION

Accordingly, it is one object of the present invention to provide aqueous detergent compositions with elevated viscosities for use in liquid cleansing agents and as the base for shampoos, bath and shower gels and other cosmetic formulations.

It is another object of the present invention to provide thickenable detergent compositions which are compatible with the skin and mucous membranes of the eyes.

These and other objects, which will become apparent during the course of the following detailed description, have been achieved by preparing aqueous mixtures of carboxymethylated ethoxylates in which the alkyl group is monounsaturated or polyunsaturated, optionally in combination with carboxymethylated ethoxylates in which the alkyl group is saturated, and electrolytes, with these mixtures optionally containing small amounts of conventional auxiliary surfactants.

Thus, one aspect of the present invention is an aqueous detergent composition of elevated viscosity consisting of a) 5 to 30 wt. % of a carboxymethylated ethoxylate of Formula (I)

$$R-O-(C_2H_4O)_n CH_2 COOM \qquad (I).$$

in which R is a monounsaturated or polyunsaturated branched or unbranched aliphatic group with 10 to 22 carbon atoms, n is an integer of 1 to 10, and M is an alkali metal, alkaline earth metal, ammonium, or alkylammonium ion;

b) 0 to 20 wt. % of a carboxymethylated ethoxylate of Formula (II)

$$R'-O-(C_2H_4O)_m CH_2 COOM' \qquad (II).$$

in which R' is a saturated, branched or unbranched aliphatic group with 10 to 22 carbon atoms, or an alkylaromatic group with 8 to 18 carbon atoms in the alkyl group, m is an integer of 1 to 10, and M' is an alkali metal, alkaline earth metal, ammonium, or alkylammonium ion;

c) 0.2 to 6 wt. % electrolyte; and d) optional auxiliary surfactants, and water to make 100 wt. %.

DETAILED DESCRIPTION OF THE PREFERRED EMBODIMENTS

The known group of substances (see U.S. Pat. No. 2,183,853) with the formula

$$R-O-(CH_2H_4O)_n CH_2 COOM,$$

in which R stands for an aliphatic or alkylaromatic group, n stands for the degree of ethoxylation, and M stands for a metal ion, can be prepared by the method of DE-OS 24 18 444 or European Patent Application 0 106 018 from the corresponding ethoxylates by reaction with chloroacetic acid, or by the method of European Patent Application 0 018 681 or DE-OS 28 16 127 by oxidation. Because of their high surface activity and their very good skin and eye mucous membrane tolerability, they have been used for some years, particularly in cosmetic formulations and also in cleansing systems [See: N. A. I. Paassen, *Seifen-Öle-Fette-Wachse*, vol. 109, 353 (1983)]. However, although the carboxymethylated ethoxylates demonstrate such attractive gentleness to the skin, they have the disadvantage of being very difficult to thicken [See: Hamke Meijer, *Seifen-Öle-Fette-Wachse*, vol. 114, 159 (1988)]. According to European Patent Application 0 176 151, the carboxymethylated ethoxylates cannot be thickened at all with electrolytes.

Carboxymethylated ethoxylates of ordinary $C_{12}/C_{14}$ fatty alcohols can in fact scarcely be thickened by NaCl or other ordinary electrolytes. When a change is made to longer hydrocarbon chains, the thickenability does increase a little, but very turbid solutions are formed. Thus, a clear, viscous (>1000 mPa×s), carboxymethylated ethoxylate of a saturated fatty alcohol thickened by electrolyte, for example, cannot by prepared in an aqueous solution that contains less than 10% surfactant.

It has now been found that, surprisingly, carboxymethylated ethoxylates based on unsaturated alcohols, or these mixed with carboxymethylated ethoxylates based on saturated alcohols, form high-viscosity, gelatinous, but completely clear aqueous systems with electrolytes as thickening agents, although the content of active detergent is only 10 wt. % and the electrolyte content is only 1–3 wt. %.

The unsaturated carboxymethylated ethoxylates used according to the present invention have Formula (I)

$$R-O-(C_2H_4O)_nCH_2COOM \qquad (I),$$

in which R stands for a linear or branched, monounsaturated or polyunsaturated hydrocarbon group with 10 to 22, preferably 12 to 20 carbon atoms, n is 1 to 10, preferably 2 to 8, and M stands for a metal ion such as a sodium, potassium, or an alkaline earth metal, or an ammonium or alkylammonium ion, preferably a sodium ion.

Another group of carboxymethylated ethoxylates optionally used pursuant to the present invention, but only in combination with compounds of Formula (I), have Formula (II)

$$R'-O-(C_2H_4O)_mCH_2COOM' \qquad (II),$$

in which R' stands for a saturated, branched or unbranched aliphatic group with 10 to 22, preferably 12 to 18 carbon atoms, or an alkylaromatic group with 8 to 18, preferably 8 to 14 carbon atoms in the alkyl group, m is 1 to 10, preferably 3 to 8, and M' stands for a metal ion such as sodium, potassium, or an alkaline earth metal, or an ammonium or alkylammonium ion, preferably a sodium ion.

These compounds are prepared, for example, by reacting fatty alcohol ethoxylates with chloroacetic acid in the presence of bases such as NaOH. The reaction is more or less quantitative, depending on the ethoxylate/chloroacetic acid ratio, so that the carboxymethylated ethoxylate used according to the present invention is frequently a mixture of ethoxylate starting material and reaction product. Depending on the intended use, the salt formed at the same time can remain in the product in many cases. Carboxymethylated ethoxylates based on oleyl alcohol, elaidyl alcohol, linoleyl alcohol, linolenyl alcohol, gadoleyl alcohol, arachidonyl alcohol, erucyl alcohol, or ricinoleyl alcohol, etc., and their mixtures are suitable, in particular, for cosmetic applications. It is preferred that the ethoxylate be based on oleyl alcohol, linoleyl alcohol, linolenyl alcohol, ricinoleyl alcohol, or a mixture thereof.

When these carboxymethylated ethoxylates with unsaturated hydrocarbon groups are used together with those having saturated hydrocarbon groups, the ratio of unsaturated compound to saturated compound should be 10:1 to 1:4, preferably 3:1 to 1:2 based on weight. The concentration in aqueous solutions should be 5 to 30, preferably 7 to 20 wt. % for compounds with an unsaturated group, and 0 to 20, preferably 2 to 10 wt. %, for those with a saturated group.

Suitable electrolytes used in the present invention are the conventional electrolyte thickeners, such as NaCl, $NH_4Cl$, $Na_2SO_4$, or $MgSO_4$, etc. The concentrations are 0.2 to 6 wt. %, preferably 0.5 to 5 wt. %.

The carboxymethylated ethoxylates used in the present invention ordinarily have sufficient foaming power with regard to their application. If higher degrees of foaming are desired, the addition of smaller amounts of strongly foaming auxiliary surfactants such as organic sulfates, sulfonates, amine oxides, amphoteric surfactants, or mixtures thereof, is recommended. The ratios by weight of these auxiliary surfactants to the carboxymethylated ethoxylates are suitably 3:7 to 1:9. In some cases, but rarely because of their environmental problems, it may be advantageous to use fatty acid amides also in small amounts for viscosity regulation.

Other additives that may be used, depending on the application, are smaller amounts of polymers such as polyethylene oxide, chelating agents, preservatives, fragrances, etc.

Other features of the invention will become apparent in the course of the following descriptions of exemplary embodiments which are given for illustration of the invention and are not intended to be limiting thereof.

EXAMPLES

The following Examples are intended to show the effective thickenability with electrolytes of the carboxymethylated ethoxylates pursuant to the present invention. This is determined by viscosity measurements using a rotational viscometer (Haake RV 20) at 25° C. at definite rates of shear. In the case of severely non-Newtonian preparations, the average viscosities at shear rates between 3 and 10 $sec^{-1}$ are reported, or in other words, under conditions that correspond approximately to the motion process when liquid flows out of a plastic bottle with a central opening. The content of active detergent in all of the examples is 10%.

EXAMPLE 1 (Pursuant to the Present Invention)

Carboxymethylated Ocenol-80/85* ethoxylate sodium salt with 3 moles of ethylene oxide/mole (degree of carboxymethylation 88%, product contains 9.8% NaCl) and additional NaCl are dissolved in water in a glass flask, and the viscosity of the solution is measured after standing for 48 h. The results are given in Table 1.

* Mixture of oleyl alcohol and cetyl alcohol from the Henkel Company.

TABLE 1

|  | Total NaCl (%) | | | |
| --- | --- | --- | --- | --- |
|  | 1 | 1.5 | 2.5 | 3.5 |
| Appearance of solution after 48 h. | Clear | Clear | Cloudy | 2 phases |
| η 25° C. (mPa × s) | 880 | 2,900 | 7,000 | — |

The results presented in Table 1 show the effective thickenability of the carboxymethylated ethoxylates of the present invention.

EXAMPLE 2 (Pursuant to the Present Invention)

Carboxymethylated Ocenol-80.85 ethoxylate, with 4 moles of ethylene oxide/mole (degree of carboxymethylation 90%, product contains 10.1% NaCl) and additional NaCl are dissolved in water and the viscosity of the clear solution is measured after standing for about 48 h. The results are given in Table 2.

TABLE 2

|  | Total NaCl (%) | | | | | | |
| --- | --- | --- | --- | --- | --- | --- | --- |
|  | 1.0 | 1.5 | 2.0 | 2.5 | 3.0 | 3.5 | 4 |
| η 25° C. (mPa × s) | 3 | 6 | 8 | 45 | 700 | 1,500 | 2,800 |

EXAMPLE 3 (Comparative Example)

Carboxymethylated Alfol-12-14 ethoxylate with 4.5 moles of ethylene oxide/mole (degree of carboxymethylation 80%, product contains 8.5% NaCl) and additional NaCl are dissolved in water and the viscosity of the clear solutions is determined. The results are given in Table 3.

TABLE 3

| | Total NaCl (%) | | | | | |
|---|---|---|---|---|---|---|
| | 2 | 4 | 6 | 8 | 10 | 12 |
| $\eta$ 25° C. (mPa $\times$ s) | 1 | 1.3 | 2.3 | 6 | 25 | 70 |

The results presented in Table 3 show that thickenability adequate for practical application is not obtained with this carboxymethylated ethoxylate with saturated aliphatic group.

EXAMPLE 4 (Comparative Example)

It was attempted to dissolve carboxymethylated Talgfett-1618 ethoxylate with 5 moles of ethylene oxide/mole (degree of carboxymethylation 91%, product contains 9.2% NaCl) in water together with additional NaCl. The liquids were cloudy with a distinct tendency toward phase separation at all NaCl concentrations, so that there is no practical application.

TABLE 4

| | Total NaCl (%) | | | |
|---|---|---|---|---|
| | 1 | 2 | 3 | 4 |
| Appearance of solution | Cloudy | Cloudy (Opalescent) | 2-Phased | |
| $\eta$ 25° C. (mPa $\times$ s) | 900 | 700 | 450 | |

EXAMPLE 5 (Pursuant to the Present Invention)

Carboxymethylated Ocenol-92/96* ethoxylate with 4 moles of ethylene oxide/mole (degree of carboxymethylation 91%, product contains 10.1% NaCl) was dissolved in water together with additional NaCl and its viscosity was measured after standing for a long time. The solutions, which were clear over the entire range of NaCl concentrations, have a gelatinous consistency at NaCl concentrations $\geq$ 3%. The results are given in Table 5.
* Oleyl alcohol from the Hendel Co.

TABLE 5

| | Total NaCl (%) | | | | |
|---|---|---|---|---|---|
| | 1 | 2 | 3 | 4 | 6 |
| $\eta$ 25° C. (mPa $\times$ s) | 5 | 25 | 1,700 | 6,500 | 7,000 |

EXAMPLE 6 (Pursuant to the present Invention)

Carboxymethylated Ocenol-110/130* ethoxylate with 4 moles of ethylene oxide/mole (degree of carboxymethylation 89%, product contains 10.0% NaCl) and additional NaCl are dissolved together in water and the viscosity of the clear solutions is measured. The results are given in Table 6.
* Oleyl-linoleyl alcohol from the Henkel Co.

TABLE 6

| | Total NaCl (%) | | | | |
|---|---|---|---|---|---|
| | 1 | 1.5 | 2 | 3 | 4 |
| $\eta$ 25° C. (mPa $\times$ s) | 2 | 8 | 130 | 2,900 | 4,800 |

EXAMPLE 7 (Pursuant to the Present Invention)

Carboxymethylated Ocenol-92.96 ethoxylate with 3.5 moles of ethylene oxide/mole (conversion 91%, product contains 10% NaCl) and NH$_4$Cl are dissolved together in water and the viscosity of the clear, sometimes gelled solutions is measured. The results are given in Table 7.

TABLE 7

| | Total NH$_4$Cl (%) | | | |
|---|---|---|---|---|
| | — | 0.5 | 1 | 2 | 3 |
| $\eta$ 25° C. (mPa $\times$ s) | 12 | 948 | 4,030 | 6,200 | 9,700 |

EXAMPLE 8 (Pursuant to the Present Invention)

Carboxymethylated Ocenol-80/85 ethoxylate with 4.5 moles of ethylene oxide/mole (conversion 90%, product contains 9.8% NaCl) and carboxymethylated C$_{16}$/C$_{18}$ tallow alcohol** ethoxylate with 5 moles of ethylene oxide/mole (conversion 91%, product contains 9.2% NaCl) are dissolved in water in a ratio by weight of 3:1 together with NH$_4$Cl. Viscosity measurements on the clear solutions show the following dependence:
** Approx. 29% C$_{16}$H$_{33}$OH, 68% C$_{18}$H$_{37}$OH

TABLE 8

| | Total NH$_4$Cl (%) | | | |
|---|---|---|---|---|
| | — | 2 | 3 | 4 | 5 |
| $\eta$ 25° C. (mPa $\times$ s) | 4 | 27 | 410 | 2,750 | 4,300 |

EXAMPLE 9 (Pursuant to the Present Invention)

Carboxymethylated Ocenol-92/96 ethoxylate with 3 moles of ethylene oxide/mole and C$_{14}$/C$_{16}$ olefin sulfonate are dissolved together in water in a ratio by weight of 4:1 together with additional NaCl. The viscosity of the clear solutions is determined after standing for 48 hours. The results are given in Table 9.

TABLE 9

| | Total NaCl (%) | | |
|---|---|---|---|
| | 1 | 2 | 3 |
| $\eta$ 25° C. (mPa $\times$ s) | 16 | 860 | 10,100 |

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. An aqueous detergent composition having a viscosity of >1,000 mPa.S, comprising
   a) 5 to 20 wt. % of a carboxymethylated ethoxylate of Formula (I)

$$R-O-(C_2H_4O)_nCH_2COOM \qquad (I)$$

wherein
R is a monounsaturated or polyunsaturated, branched or unbranched aliphatic group with 10 to 22 carbon atoms,
n is an integer of 1 to 10, and M is an alkali metal, alkaline earth metal, ammonium, or alkylammonium ion;

b) 0 to 10 wt. % of a carboxymethylated ethoxylate of Formula II $$R'-O-(C_2H_4O)_mCH_2COOM' \qquad (II)$$

wherein

R is a saturated, branched or unbranched aliphatic group with 10 to 22 carbon atoms, or an alkylaromatic group with 8 to 18 carbon atoms in the alkyl group, m is an integer or 1 to 10, and M' is an alkali metal, alkaline earth metal, ammonium, or alkylammonium ion;

c) 1 to 6 wt. % of an electrolyte selected from the group consisting of NaCl and NH₄Cl; and d) water, to make 100 wt. %.

2. The aqueous detergent composition of claim 1, further comprising an auxiliary surfactant.

3. The aqueous detergent composition of claim 2, wherein said auxiliary surfactant is selected from the group consisting of organic sulfates, organic sulfonates, amine oxides, amphoteric surfactants, and mixtures thereof.

4. The aqueous detergent composition of claim 1, wherein in said carboxymethylated ethoxylate of Formula (I), R is selected from the group consisting of oleyl, linoleyl, linolenyl, ricinoleyl, and mixtures thereof.

5. The aqueous detergent composition of claim 1, wherein in said carboxymethylated ethoxylate of Formula (I), n is an integer of 2 to 8 and M is sodium.

6. The aqueous detergent composition of claim 1, wherein in said carboxymethylated ethoxylate of Formula (II), R' is a saturated, branched, or unbranched aliphatic group with 12 to 18 carbon atoms, or an alkylaromatic group with 8 to 16 atoms in the alkyl group.

7. The aqueous detergent composition of claim 1, wherein in said carboxymethylated ethoxylate of Formula (II), m is an integer of 3 to 8 and M' is sodium.

8. The aqueous detergent composition of claim 1, wherein the amount of said carboxymethylated ethoxylate of Formula (I) is 7 to 20 wt. %.

9. The aqueous detergent composition of claim 1, wherein the amount of said carboxymethylated ethoxylate of Formula (II) is 2 to 10 wt. %.

10. The aqueous detergent composition of claim 1, wherein the amount of said electrolyte is 1 to 5 wt. %.

11. The aqueous detergent composition of claim 1, wherein the ratio of the amount of said carboxymethylated ethoxylate of Formula (I) to the amount of said carboxymethylated ethoxylate of Formula (II) is from 10:1 to 1:4.

12. The aqueous detergent composition of claim 11, wherein the ratio of the amount of said carboxymethylated ethoxylate of Formula (I) to the amount of said carboxymethylated ethoxylate of Formula (II) is from 3:1 to 1:2.

13. A shampoo, bath gel, shower gel or cleansing agent, comprising an aqueous detergent composition having a viscosity of >1,000 mPa.S, comprising a) 5 to 20 wt. % of a carboxymethylated ethoxylate of Formula (I)

$$R-O-(C_2H_4O)_nCH_2COOM \qquad (I)$$

wherein

R is a monounsaturated or polyunsaturated, branched or unbranched aliphatic group with 10 to 22 carbon atoms, n is an integer of 1 to 10, and M is an alkali metal, alkaline earth metal, ammonium, or alkylammonium ion;

b) 0 to 10 wt. % of a carboxymethylated ethoxylate of Formula II $$R'-O-(C_2H_4O)_mCH_2COOM' \qquad (II)$$

wherein

R' is a saturated, branched or unbranched aliphatic group with 10 to 22 carbon atoms, or an alkylaromatic group with 8 to 18 carbon atoms in the alkyl group, m is an integer or 1 to 10, and M' is an alkali metal, alkaline earth metal, ammonium, or alkylammonium ion;

c) 1 to 6 wt. % of an electrolyte selected from the group consisting of NaCl and NH₄Cl; and d) water, to make 100 wt. %.

* * * * *